US010639402B2

(12) United States Patent
Saleh et al.

(10) Patent No.: US 10,639,402 B2
(45) Date of Patent: May 5, 2020

(54) TITANIUM-BASED FUNCTIONAL NANO-ARCHITECTURES FOR DRUG ELUTING STENTS

(71) Applicant: The American University in Cairo, New York, NY (US)

(72) Inventors: Yomna Emad Saleh, New Cairo (EG); Mohamed Abdel-Hady Gepreel, Alexandria (EG); Nageh K. Allam, New Cairo (EG)

(73) Assignee: The American University in Cairo, New York, NY (US)

( * ) Notice: Subject to any disclaimer, the term of this patent is extended or adjusted under 35 U.S.C. 154(b) by 0 days.

(21) Appl. No.: 15/588,428

(22) Filed: May 5, 2017

(65) Prior Publication Data

US 2017/0296705 A1 Oct. 19, 2017

Related U.S. Application Data

(63) Continuation-in-part of application No. 15/365,276, filed on Nov. 30, 2016.

(60) Provisional application No. 62/262,685, filed on Dec. 3, 2015.

(51) Int. Cl.
*A61F 2/82* (2013.01)
*A61L 31/02* (2006.01)
*A61L 31/14* (2006.01)

(52) U.S. Cl.
CPC ............ *A61L 31/022* (2013.01); *A61L 31/14* (2013.01); *A61L 2400/12* (2013.01); *A61L 2400/18* (2013.01)

(58) Field of Classification Search
CPC ........................................................ A61F 2/82
See application file for complete search history.

(56) References Cited

U.S. PATENT DOCUMENTS

2006/0229715 A1* 10/2006 Istephanous .......... A61F 2/0077
623/1.46
2007/0032862 A1* 2/2007 Weber ...................... A61F 2/82
623/1.34

OTHER PUBLICATIONS

Shape Memory Effect in New Ti—Nb—Ta Alloy Material Science Forum, ISSN: 1662-9572, vol. 889, pp. 165-170.

* cited by examiner

*Primary Examiner* — Matthew W Schall
(74) *Attorney, Agent, or Firm* — Lumen Patent Firm

(57) ABSTRACT

A drug eluting stent is provided that includes a Ni-free Ti-17Nb-6Ta stent, and Ti-17Nb-6Ta oxides nanotubes grown on an inner wall of the Ti-17Nb-6Ta stent, where the Ti-17Nb-6Ta oxides nanotubes are configured for holding and releasing drugs to enable enhanced endothelialization for better healing.

6 Claims, 13 Drawing Sheets

TITANIUM-BASED FUNCTIONAL NANO-ARCHITECTURES FOR DRUG ELUTING STENTS

CROSS-REFERENCE TO RELATED APPLICATIONS

This application is a continuation-in-part of U.S. patent application Ser. No. 15/365,276 filed Nov. 30, 2016, which is incorporated herein by reference. U.S. patent application Ser. No. 15/365,276 filed Nov. 30, 2016 claims priority from U.S. Provisional Patent Application 62/262,685 filed Dec. 3, 2015, which is incorporated herein by reference.

FIELD OF THE INVENTION

The present invention relates generally to medical stents. More particularly, the invention relates to a nanoarchitectural system as surface enhancement for drug eluting stents.

BACKGROUND OF THE INVENTION

Coronary heart disease (CHD) is the leading cause of death worldwide for both genders, especially in high and middle-income countries. It has been intrinsically associated with atherosclerosis since the beginning of the $20^{th}$ century. Pathologically, atherosclerosis is characterized by the formation of localized plaques within arterial walls which hinder normal blood flow. When atherosclerotic plaques are localized in one or more coronary arteries—known as coronary artery disease (CAD)—they prevent sufficient flow of oxygenated blood to the heart muscles. This results in an ischemic state at the heart muscle causing symptomatic events that range from angina pectoris to myocardial infarction, which ultimately result in sudden death.

For a long time, coronary artery bypass graft (CABG) remained the gold standard practice for the treatent of coronary artery disease. However, CABG involves an invasive intervention in order to bypass blocked artery using a graft harvested from other body parts. In 1977, the first percutaneous transluminal coronary angioplasty (PTCA) was performed to replace CABG as a minimally invasive technique, which spares CAD patients post-surgical risks and complications. With plain balloon angioplasty, it was noticed that post-procedural arterial response involved 5% risk of acute restenosis during the first 24 hours, or 20-50% risk of late occlusion during the first six months, due to elastic recoiling of arterial smooth muscles. Accordingly, placement of intracoronary stents became rapidly the method of choice for PTCA to act as a residing scaffold preventing arterial collapse incurred by plain balloon angioplasty. Furthermore, drug eluting stents were introduced to avoid neointimal hyperplasia caused by Bare Metal Stents (BMS). They decreased vessel restenosis rates from 20-30% with BMS to below 10-18%, revolutionizing the field of coronary intervention. By 2006, 8 out of 10 deployed coronary stents were DES, at an annual cost between 4 billion to 5 billion USD. Clinical evaluations have so far showed strong evidence of DES superiority over BMS in reduction of in-stent restenosis rates. However, cases of serious clinical events have raised concerns over DES long time safety and efficiency. In particular, risks of late and very late stent thrombosis. Several proposals have been offered to explain why such technical marvels would turn to be thrombogenic. Some of the most supported reasons are; 1) delayed endothelialization due to locally delivered cytotoxic or cytostatic drugs or other pathological risk factors, 2) inherent thrombogenicity of the stent as a foreign body to blood circulation, 3) hypersensitivity reactions related to the metallic material used for stent manufacturing or/and polymeric coatings used as drug carriers, 4) Dual Antiplatelet Therapy (DAPT) early discontinuation, and 5) stent malapposition or incomplete apposition, related to technical deployment.

A wide range of different materials have been previously used in the manufacturing of stents. These materials need to fulfill rigorous mechanical, physical and, chemical properties. According to procedure of implantation, long term application and safety, these properties are strongly studied and directly affect the choice of the stent. Titanium (Ti) and its alloys have been widely used in biomedical field especially in dental and orthopedic applications. They show excellent biocompatibility and high corrosion resistance due to the oxide layer formed on their surface, which is highly stable. However, for coronary stent manufactory, Ti application has been limited to bio-inert coatings that showed significantly reduced thrombogenicity and intimal hyperplasia, such as Ti-nitride-oxide layer on Titan© stent (Hexacath, France). The reason why pure titanium or some of its common alloys have not been used as stent materials is due to their high yield strength and relatively low tensile strength. Therefore, during deployment with balloon expansion, they will need to expand to stresses greater than their yield strength. Also, with the low tensile strength and low ductility, the stent will be easily prone to fracture. Alloying Ti with materials that would reduce its yield strength might be a good strategy to make it mechanically acceptable, while keeping original tensile strength. Some of the promising Ti-alloys for making stents are those containing Ta and Ni. Also, Ni—Ti alloys are extensively used in stents manufacturing, specially for self-expandabe stents. However, Ni-hypersensitivity and toxicity have stimulated the development of Ni-free Ti-based shape memory alloys.

Coatings have been initially used to enhance the biocompatibility of stent materials within vascular environment. Later, they were used as vehicle for drug loading and a platform to offer advanced solution for better endothelialization. However, using a different materials for coating, whether polymeric or metallic, can add a layer of complexity within the manufacturing process and more importantly can be mechanically questionable during application. Mechanical disturbance at the interface between the coating and substrate can occur due to crystal mismatch.

What is needed is a nanoarchitecture that is self-grown on a newly designed Ni-free alloy for DES surface treatment, that have mechanical properties that are comparable to Nitinol, which is currently the most widely used material for self-exandable stents, and has enhanced surface self-grown from the substrate material to avoid surface coating and crystal mismatch.

SUMMARY OF THE INVENTION

To address the needs in the art, a drug eluting stent is provided that includes a self expandable Ni-free Ti-17Nb-6Ta stent, and Ti-17Nb-6Ta oxides nanotubes grown on an inner wall of the Ti-17Nb-6Ta stent, where the Ti-17Nb-6Ta oxides nanotubes are configured for holding and releasing drugs to enable enhanced endothelialization for better healing.

According to one embodiment of the invention, the Ti-17Nb-6Ta oxides nanotubes are organized in a vertical orientation relative to the inner wall of the Ti-17Nb-6Ta stent.

In a further aspect of the invention, the Ti-17Nb-6Ta stent is a self-expanding Ti-17Nb-6Ta stent.

In another aspect of the invention, the Ti-17Nb-6Ta oxides nanotubes have an inner diameter in a range of 65 nm to 85 nm.

In yet another aspect of the invention, the Ti-17Nb-6Ta oxides nanotubes have a length in a range of up to 14 µm.

According to one aspect of the invention, the self expandable Ti-17Nb-6Ta stent and the Ti-17Nb-6Ta oxides nanotubes are Ni-free and biocompatible and non-toxic to a human host.

DETAILED DESCRIPTION

Figure 1A:
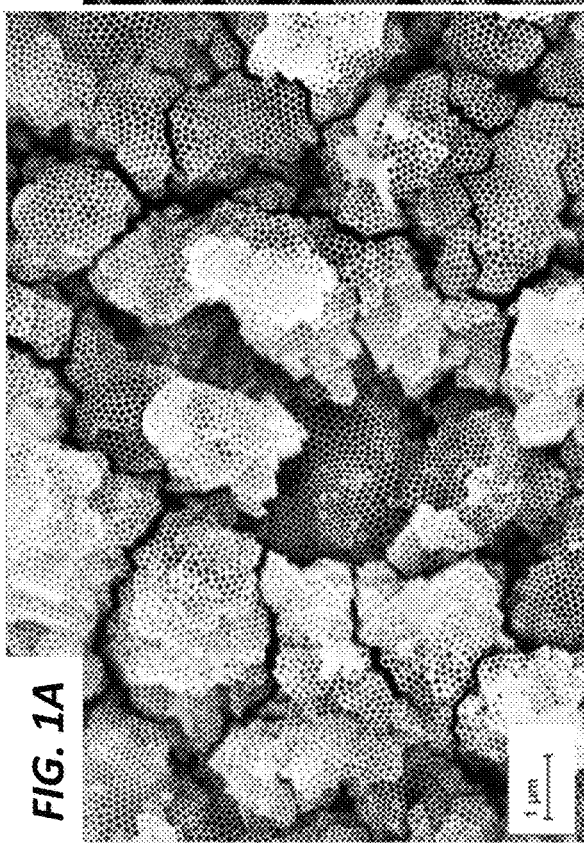
FIGS. 1A-1D show FESEM images of as-anodized Ti-17Nb-6Ta oxides with no post thermal treatment after cold rolling. (1A) Low magnification top-view image of the highly ordered, vertically oriented NTs, with different lengths, (1B) high magnification top-view image of the homogenous NTs, (1C) and (1D) side views of NTs detached layers, showing NTs bottom side at low and high magnifications, respectively, according to the current invention.
Figure 1B:
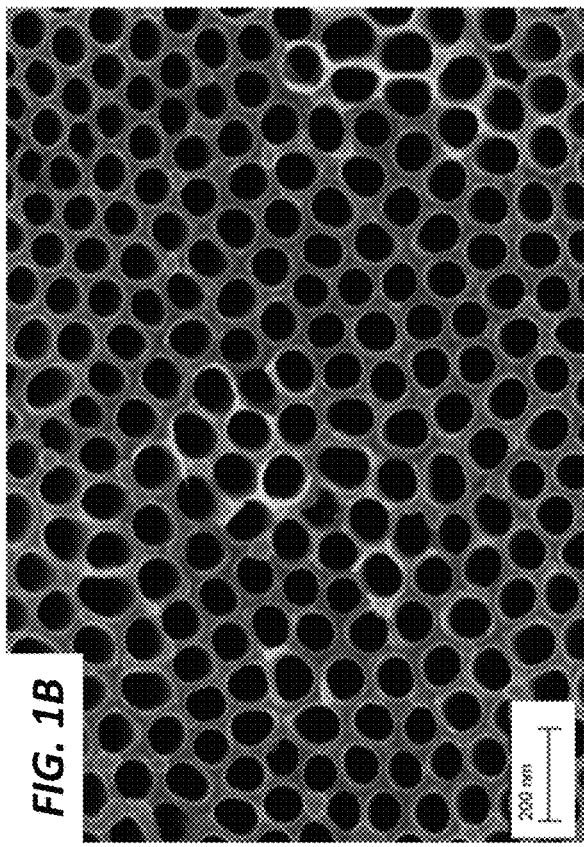
Figure 1C:
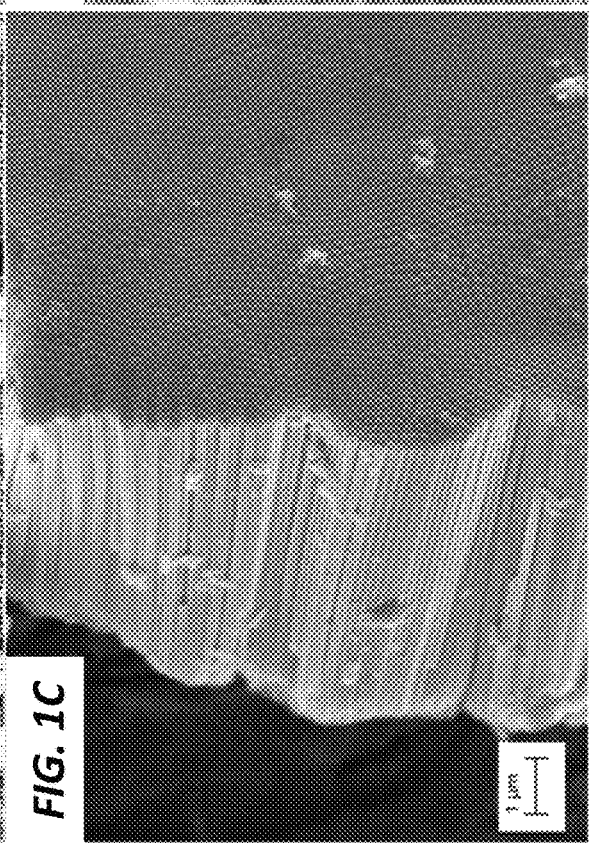
Figure 1D:
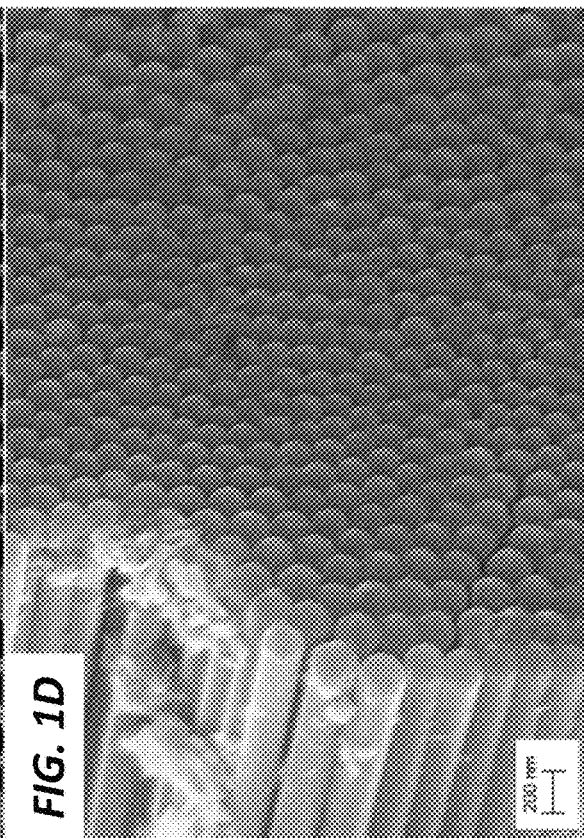

Different strategies have been investigated to allow for optimum duration and conditions for endothelium healing through the enhancement of coronary stents. The current invention provides a nanoarchitectured system that includes a surface modification for drug eluting stents. In one exemplary embodiment, oriented nanotubes are vertically grown on the surface of a new Ni-free biocompatible Ti-based alloy, as a material for self-expandable stents. The fabricated nanoarchitectured system was self-grown from the potential stent substrate. This material is also configured to enhance endothelial proliferation while acting as drug reservoir to hinder Vascular Smooth Muscle Cells (VSMC) proliferation. Two morphologies were prepared to demonstrate the effect of structure homogeneity on the intended application. They were characterized by field-emission scanning electron microscope (FESEM), X-ray diffraction (XRD), Raman spectroscopy, energy dispersive X-ray spectroscopy (EDX), and X-ray photoelectron spectroscopy (XPS). Nanoindentation technique was used to study the mechanical properties of the fabricated material. Cytotoxicity and proliferation studies were done and compared for the two fabricated nanoarchitectures versus smooth untextured samples using in-vitro cultured endothelial cells. Finally, drug loading capacity was investigated practically and supported by computational study of release profile using COMSOL Multiphysics software.

The current invention uses a new Ti-17Nb-6Ta alloy having a Young's modulus of 68 GPa, ultimate tensile strength (UTS) of 700-1050 MPa, Elongation of 10-30% and corrosion resistance of −44.1 Ecorr (mV). Furthermore, the tantalum content enhances radio-opacity and stent visibility during PCTA due to its relatively high density. Two different nanomorphologies were fabricated to demostrate the effect of structure homogenity in the intended application.

In one embodiment, Ammonium fluoride (ACS reagent, ≥98.0%), Formamide (purum, ≥98.0% (T)), Glycerol (ACS reagent, ≥99.5%), Ethylene Glycol (Pure P.A.), Ammonium Sulphate (Ex-Pure), 2'-Deoxyadenosine drug (99%) and phosphate-buffered saline (PBS, 1×) sterile liquid were obtained. The new allow was fabricated, where Ti-17Nb-6Ta buttons were prepared by arc-melting in high purity argon gas atmosphere. It was then homogenized at 1000° C. for 7.2 ks in same atmosphere. Subsequently, samples underwent cold-rolling by >95% thickness reduction (CR) to produce sheets of thickness 0.3 mm.

Prior to the anodization, Ti-alloys sheets were cleaned ultrasonically in acetone then ethanol then distilled water. Platinum foil was washed in dilute HCl then distilled water. A two-electrode electrochemical cell was used for anodization with the alloy sheet as the positive electrode and Pt sheet as the negative electrode. Two different sets of conditions were used: 1-glycerol-based electrolyte containing 0.35 M $NH_4F$+5 vol % $H_2O$+20 vol % Formamide at 50 V for 2 h, and 2-aqueous-based electrolyte containing 0.11 M NH$_4$F+1 M (NH$_4$)$_2$SO$_4$ at 40 V for 2 h. After anodization, samples were ultrasonically cleaned and left to dry in air.

Images were obtained for morphological characterization using Field emission scanning electron microscope (FE-SEM, Leo Supra 55—Zeiss Inc., operated at 9.00 kV). Morphological imaging was used to detect successful fabrication of nanoarchitecture, nanoindentation and cell proliferation on different morphologies. Only samples with fixed cell culture are gold-sputtered before imaging for better visuals.

Three techniques were used to identify and confirm structure and/or composition of the fabricated NTs layer on Ti-17Nb-6Ta alloy: (1) XRD diffractometer (D8, Brucker) with a copper tube of 1.54 Å wavelength. (2) High performance Raman Analyzer (ProRaman-L) with an excitation laser beam, wavelength of 532 nm. (3) X-ray photoelectron spectroscopy (XPS) on a Thermo Scientific K-alpha XPS with an Al anode. Spectra charged at 532 eV reference to O 1s.

Young's modulus and hardness of the anodized samples were measured before and after annealing at 450° C. for 3 hours. Tests were done using Nano Indenter XP, MTS with Berkovitch tip (20 nm) creating 6×6 array of indentations, separated by 150 μm. Nanoindentation was done with CSM Tip Calibration mode, strain 0.05 S$^{-1}$, depth 3000 nm and strain rate 10 nm/sec. FESEM was used to image the indentation projected contact area caused by the Berkovitch tip.

For biological assessment, vascular endothelial cells were extracted from mice umbilical cords and cultured in-vitro. No live vertebrates or human subjects were used in the experiments. The cells were used for cytotoxicity measurements, cells adhesion and proliferation on NTs. For cytotoxicity testing, MTT viability assay was conducted, using 96-well tissue culture plate with 10$^4$/well. Cells were incubated at temperature 37° C. with 5% CO$_2$ in a humidified incubator for 24 hours. Absorbance was measured with microplate reader (ROBONIK™ P2000 Eliza plate reader) at 570 nm. For cell proliferation, three tests were used to study the effect of nanoarchitecture on tissue healing versus smooth muscle at intervals of 1, 3 and 7 days. They were furthermore used to study the effect of structure homogeneity on cells proliferation; (1) MTT viability assay mentioned earlier, (2) imaging under FESEM after gold sputtering and (3) Trypan blue assay to count viable cells.

For drug loading, Ti-alloy sheets of 1 cm$^2$ were immersed in 2'-deoxyadenosine solution (1 mg/ml) and left for 36 hours. Sheets were then removed and left to dry in air for 12 hours. Each sheet was immersed in a 10 ml beaker containing 10 ml PBS under magnetic stirring for 3 minutes at 700 rpm. Sample from the PBS solution was withdrawn and its absorbance was measured using CARY 500 UV-Vis-NIR spectrophotometer at 260 nm to calculate the drug concentration. Drug release profiles from the NTs were theoretically predicted using computational simulation. The model was built using COMSOL Multiphysics modeling software. To simulate the kinetics of drug release from the NTs, "Transport of diluted species" module was used, with Fick's law equation governing the drug motion: ($N_i = -D_i \nabla c_i$, where for species $i$, $N_i$=the molar flux (mol m$^2$/s), $D_i$=the diffusion coefficient (m$^2$/s), and $c_i$=the concentration (mol/m$^3$)). Boundary conditions assumed that flux outside the boundaries of the NTs and the tissue is equal to zero.

Anodization was done for samples with no thermal treatment history post preparation. After samples were cold rolled, they were directly anodized in attempt to avoid the oxide layer formation without the need for sample polishing.

Upon optimizing the anodization conditions, highly ordered, vertically oriented nanotubes (NTs) were successfully self-grown on Ti-17Nb-6Ta substrate, as shown in FIGS. 1A-1D. Anodization in organic electrolyte resulted in the formation of closely packed NTs with uniform diameters assembled into honey-comb-like islands separated by grooves with fused walls at the surface. The side view image of a detached layer showed highly defined NTs with distinct, uniform walls that are free from circumferential serration. Those NTs will be named Homo-NTs throughout this disclosure. The Homo-NTs have average inner diameter of 75±5 nm and length of 12 μm. These Homo-NTs were studied for enhancing drug eluting stents by enhancing the material biological response and drug loading capacity as will be discussed in the following sections.

Figure 2B:
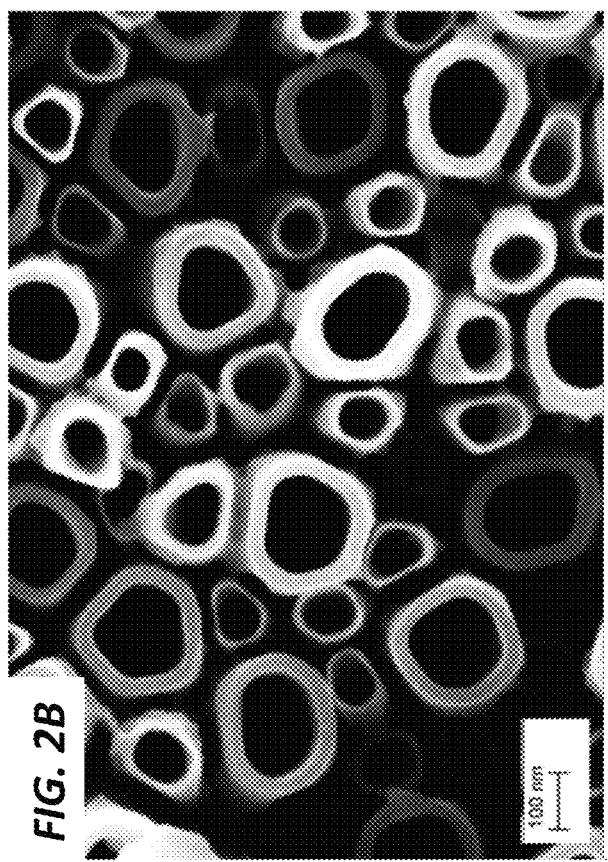
FIGS. 2A-2B show top-view FESEM images of as-anodized Ti-17Nb-6Ta sheets in aqueous electrolyte. (2A) and (2B) show the heterogeneous NTs dimensions at low and high magnifications, respectively, according to embodiments of the current invention.
Figure 2A:
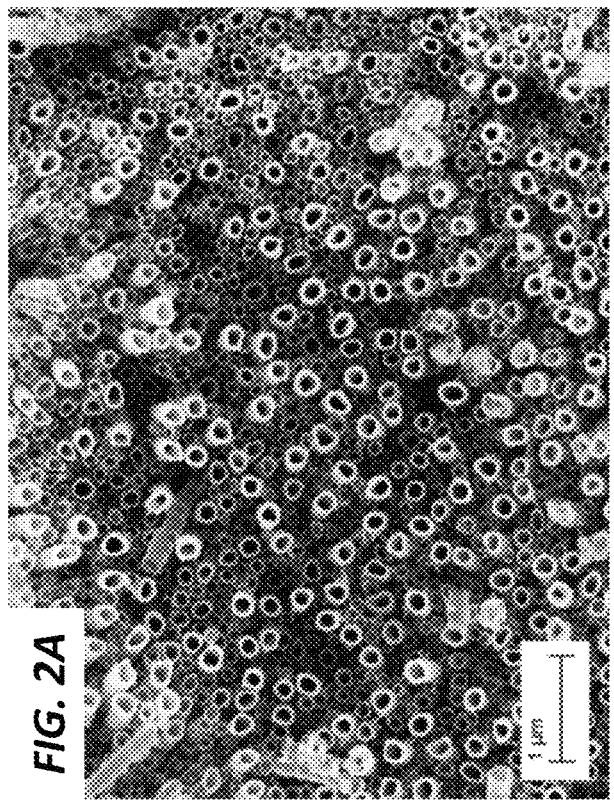

Upon anodizing the all Ti-17Nb-6Ta alloy in aqueous electrolyte containing 0.11 M NH$_4$F+1 M (NH$_4$)$_2$SO$_4$ at 40 V for 2 h, heterogeneous NTs (Hetero-NTs), with various inner diameters (80-190 nm) and wall thicknesses (6-28 nm), were obtained, as shown in FIGS. 2A-2B. However, the length of the NTs layer was found to be ~12 μm. The effect of surface morphology (Homo versus Hetero-NTs) was studied for endothelial tissue biological response and system capacity to load therapeutic agents for drug eluting stents. With almost similar layer length for the two morphologies (~12 μm), this variable was excluded from the comparison.

Figure 3:
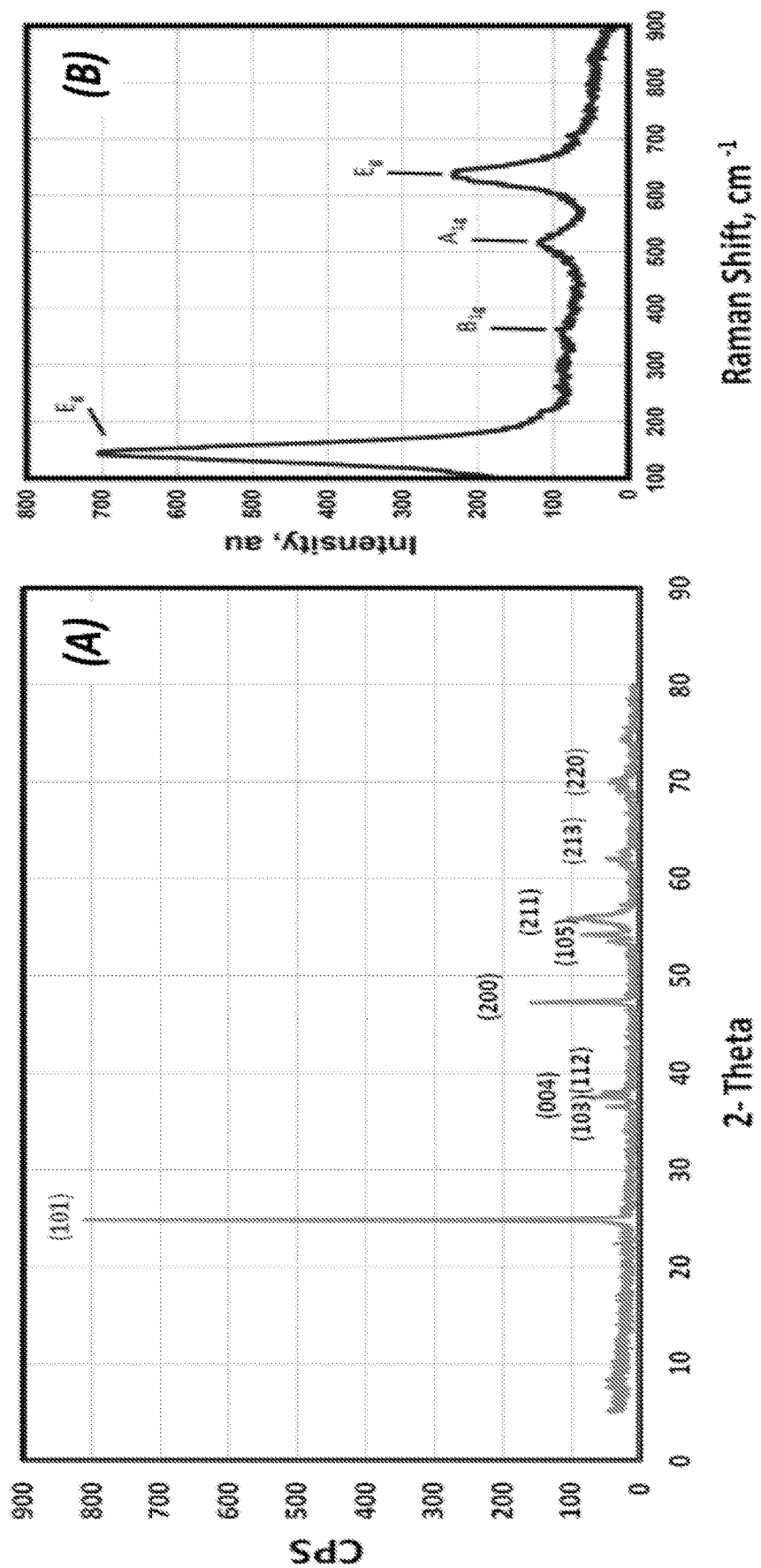
FIGS. 3A-3B: (3A) X-ray diffraction pattern and (3B) Raman spectra of Ti-17Nb-6Ta oxides surface NTs annealed at 450° C. for 3 hours, according to the current invention.

Composition and crystallinity of the fabricated Ti-17Nb-6Ta oxides NTs samples were examined using X-ray diffraction (XRD) and Raman spectroscopy after annealing at 450° C. FIG. 3A confirms the crystallization of the nanotubes in the anatase phase, with peaks corresponding to (101), (103), (004), (112), (200), (105), (211), (213) and (220) facets. These peaks are normally indicative of Titania NTs anatase phase as reported in literature. However, the absence or existence of the other alloy components, i.e. Nb and Ta oxides, cannot be confirmed nor denied from these results. It was reported that both Nb and Ta oxides existence with Titania may not alter greatly nor postpone its phase transformation to anatase. Annealed Ti—Nb, Ti—Ta—Zr and Ti—Ta surface NTs at 450° C. showed similar diffraction pattern, indicating possible overlapping of peaks from the three other components.

FIG. 3B shows the corresponding Raman spectra, indicating the tetragonal vibration mode symmetries associated with anatase; $E_g$, $E_g$, $B_{1g}$ and $A_{1g}$ modes. However, slight shift and broadening of some peaks may be indicative for the presence of other elements in the crystal. Yet, no distinctive peaks were revealed for Nb or Ta oxides. More sensitive and accurate technique was, therefore, needed for confirming or denying the formation of mixed oxides on the anodized surface. The three alloying elements have different activities towards etching and evidence was then needed to make sure that the three elements were retained during anodization and within the NTs. Accordingly, X-ray Photoelectron Spectroscopy (XPS) was used, which is considered a powerful tool for identifying surface components, chemical composition and oxidation state.

FIGS. 4A-4D show the XPS spectra of the as-anodized Ti-17Nb-6Ta samples, showing (4A) two peaks at 464.6 eV and 458.7 eV that can be assigned to Ti $2p_{1/2}$ and Ti $2p_{3/2}$, with spin orbit splitting (Δ) of 5.9 eV associated with Ti$^{4+}$. Panel (4B) revealed Nb 3d doublet at 210.98 eV and 208.08 eV associated with Nb $3d_{3/2}$ and Nb $3d_{5/2}$, with spin orbit splitting (Δ) of 2.9 eV, confirming that signals correspond to Nb$^{5+}$ exist. Panel (4C) showed a peak at 29.08 eV for Ta $4f_{5/2}$, and a peak at 27.18 eV for Ta $4f_{7/2}$, with spin orbit splitting (Δ) of 1.9 eV, confirming the presence of Ta$^{5+}$.

Finally, panel (4D) shows singlet peak at 530.98 eV corresponding to O1s, indicating the formation of metal oxide.

Figure 4:
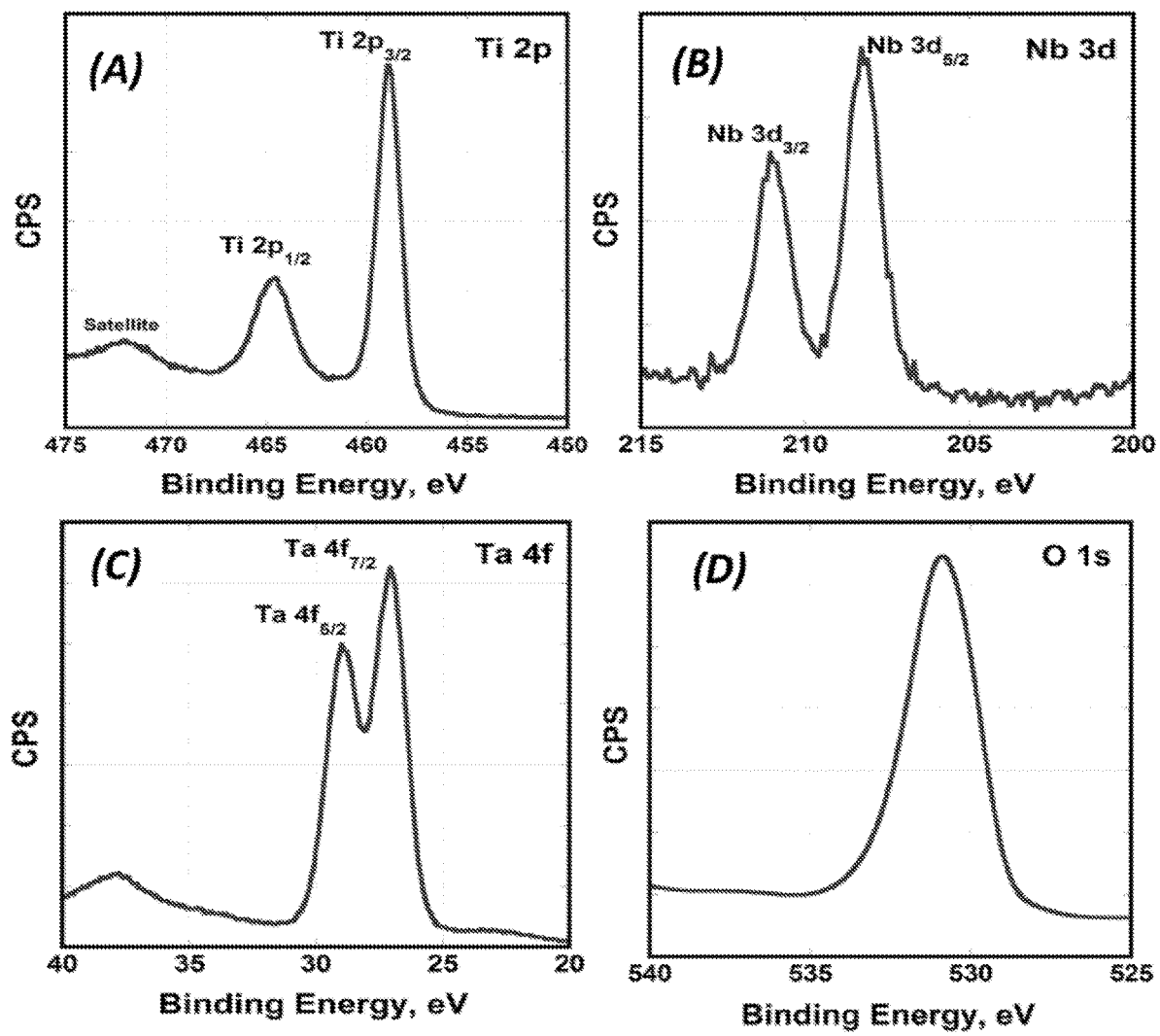
FIGS. 4A-4D show high resolution XPS spectra of (a) Ti 2p, (b) Nb 3d, (c) Ta 4f and (d) O 1s emissions for as-anodized Ti-17Nb-6Ta oxides nanotubes, according to the current invention.
Figure 5:
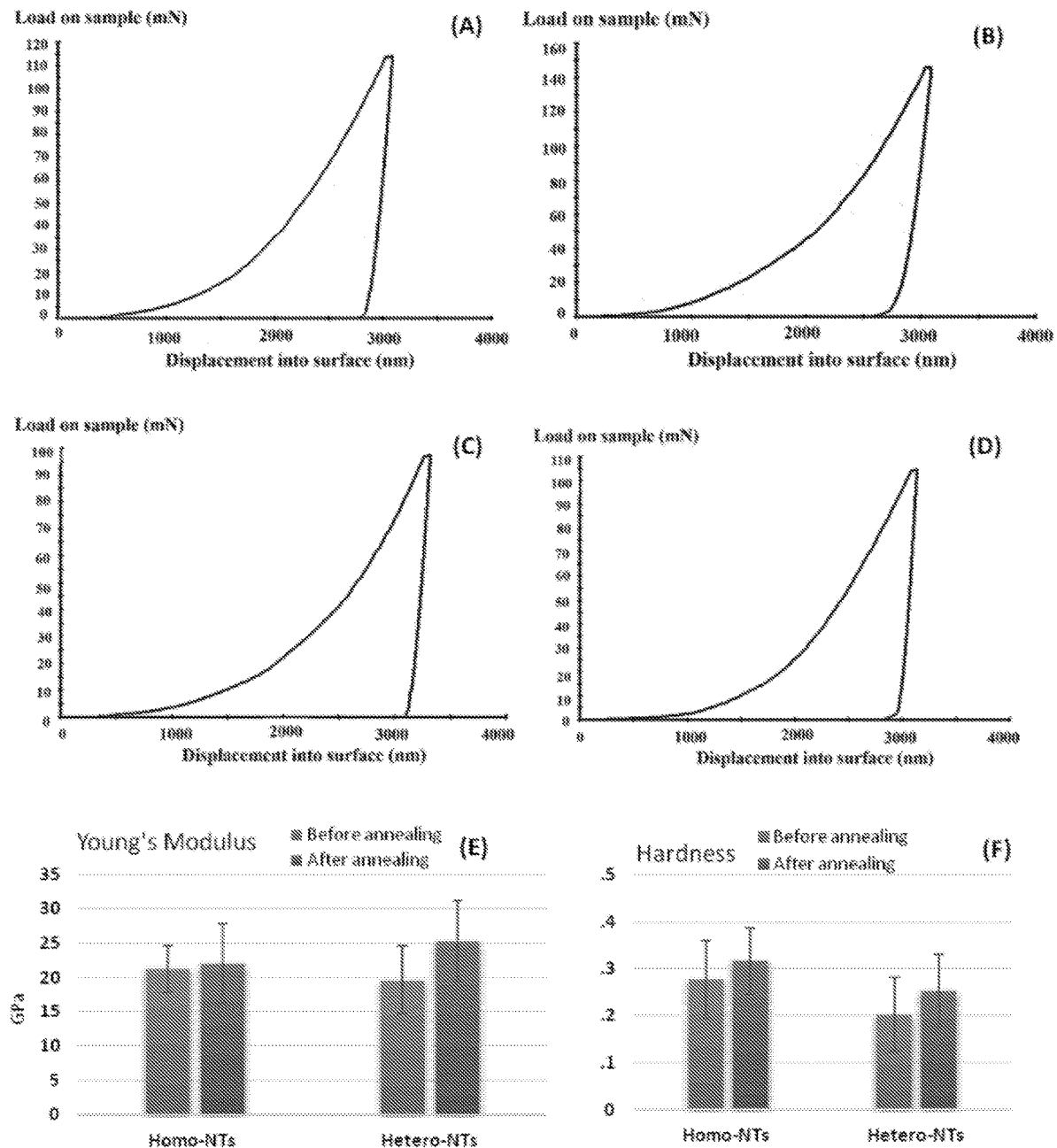
FIGS. 5A-5F show average load-displacement curves from nanoindentation of (5A), (5B) Homo-NTs and (5C), (5D) Hetero-NTS, before and after annealing respectively. (5E,5F) Young's modulus and hardness values for Homo- and Hetero-NTs, before and after annealing, according to the current invention.

Not only are the stent bulk mechanical properties critical for drug eluting stents, but also the biological interaction with material surfaces is sensitive to mechanical properties at the stent/tissue interface. Surface stiffness was found to significantly influence cells fate. The mechanical properties of the fabricated nanoarchitectures were investigated using the nanoidintation technique. The nanoidintation tip was used to estimate Young's modulus (a measure of stiffness) and hardness values, before and after annealing. During loading and unloading, hysteresis loop was observed, which indicated that NTs surface has elastic energy dissipation, as seen in FIGS. 4A-4D. Note that the elastic recovery is higher for the annealed sample (FIG. 4B and FIG. 4D compared to the as-anodized counterpart. Also, the unloading slopes of the annealed samples are found to be steeper indicating higher stiffness. The total depth of indentation is much smaller than the NTs layer thickness (12 µm). Accordingly, insights on the plastic deformation behavior of the NTs can be gained without interference from the substrate material. Young's modulus and hardness average values were calculated and compared for Homo- and Hetero-NTs before and after annealing, FIG. 5E and FIG. 5F. It was found that both Young's modulus and hardness increase with annealing for both Homo- and Hetero-NTs. This can be related to phase transformation upon annealing. For hardness, Homo-NTs were found to be superior. For Young's modulus, Homo-NTs showed lower values, which does not indicate inferiority within intended application.

Figure 6:
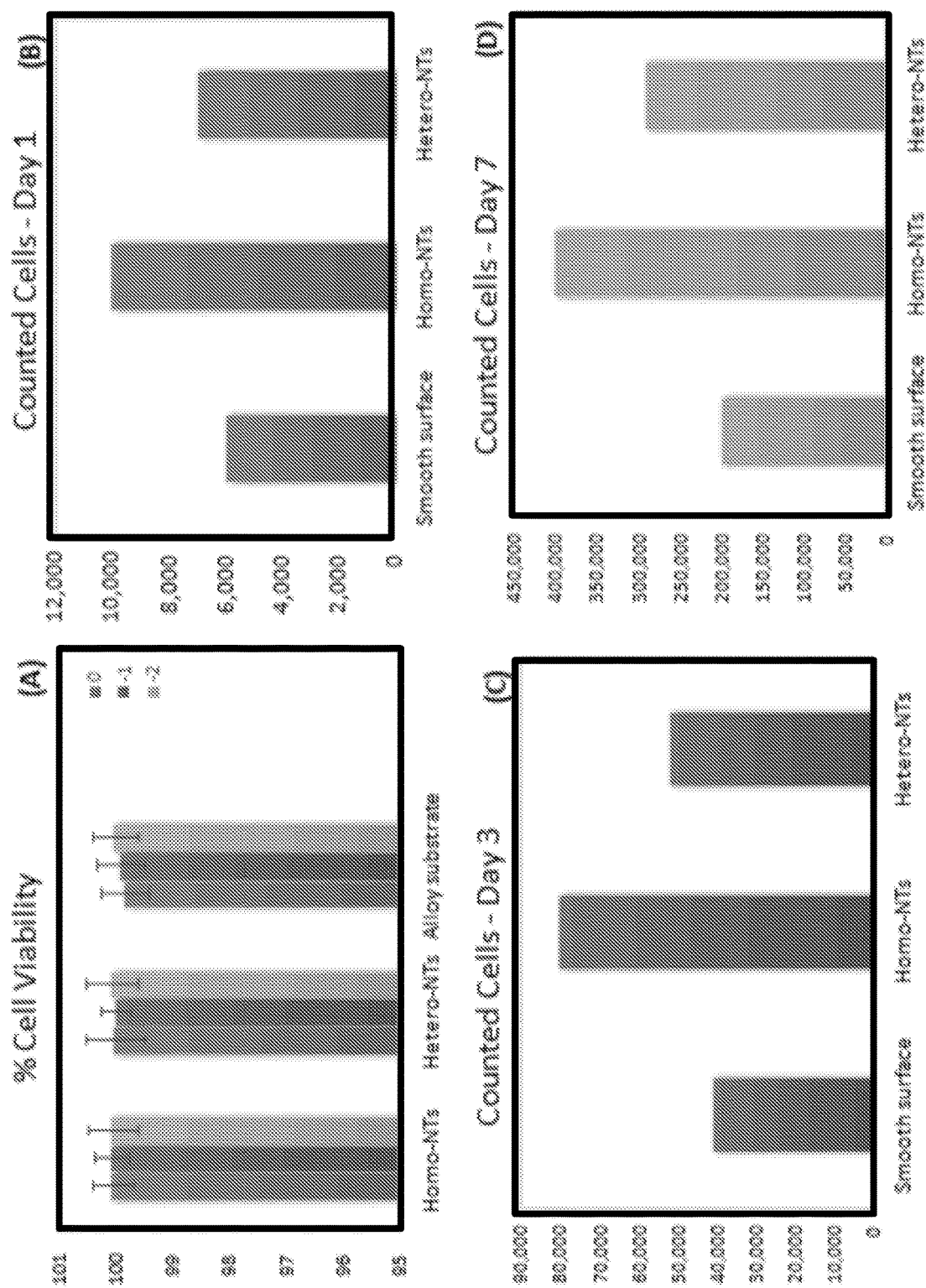
FIGS. 6A-6D show (6A) Mean values of percentage of cell viability for 1) anodized Ti-17Nb-6Ta sheets with Homo-NTs, 2) with Hetero-NTs structures and 3) as received substrate. Illustrated for each sample, values for three different dilutions (0, −1, −2) of tested samples extracts; (6B-6D) show viable endothelial cells count on 1) Ti-17Nb-6Ta smooth surface 2) with Homo-NTs, 3) with Hetero-NTs structures at different time intervals (1, 3 and 7 days), according to embodiments of the current invention.

For drug eluting stents applications, material stability and cytotoxicity are considered crucial. The use of materials with any inflammatory effect can cause local tissue sensitization, which can directly affect the healing process as well as the local thrombogenicity. FIG. 6A shows the percentage of cells survival rate or cell viability from the MTT assay for 1) Ti-17Nb-6Ta sheets with as-anodized Homo-NTs, 2) with Hetero-NTs structures, and 3) as-received substrate material. The data show three different dilutions for each sample's extract (0, −1, −2). Note that the cells' survival rate is extremely high for all samples at different dilutions, which excludes possible cytotoxicity from electrolyte after the sample cleaning post anodization. These results are in strong agreement with the biocompatibility and hemocomatability reports in literature for Titanium and Titanium alloys. Such high degree of biocompatibility is attributed to the ability of Ti-based alloys to form a stable oxide layer in most environments. Furthermore, the thicker and more stable the oxide layer, the better the material bioactivity is. This has driven earlier attempts to increase biocompatibility and activity of material surfaces by increasing the oxide layer through anodization technique.

The three different samples underwent trypan blue viability assay. For each sample both dead and viable cells were counted under the microscope at specific time intervals of 1, 3 and, 7 days. Counted viable cells of the three samples are illustrated and compared, FIGS. 6B-6D. Note that the nanoarchitectures directed better proliferation of endothelial cells than smooth surface of the material substrate at the three studied time intervals. This indicates that surface modification of drug eluting stents with nanotopography would guide faster endothelial healing. Therefore, replacing the DES polymeric coating with NTs can be of great potential towards better stenting outcome in terms of biological response. This shall not only spare the local inflammation that may be caused by polymers, but also promote endothelial tissue proper healing. Furthermore, the effect of surface homogeneity was investigated, where Homo-NTs clearly showed higher number of counted cells than Hetero-NTS, indicating better proliferation. This signifies the importance of NTs optimization in terms of dimensional homogeneity, which should be considered for the applications involving tissue regeneration. During endothelialization, nanoarchitectures temporarily mimic extracellular matrix (ECM), guiding and nurturing cells growth. The superior outcome from Homo-NTs may be attributed to better distribution of ions, proteins and nutrients required for the growth, as well as more structured spatial guidance of the cells to grow.

Figure 7:
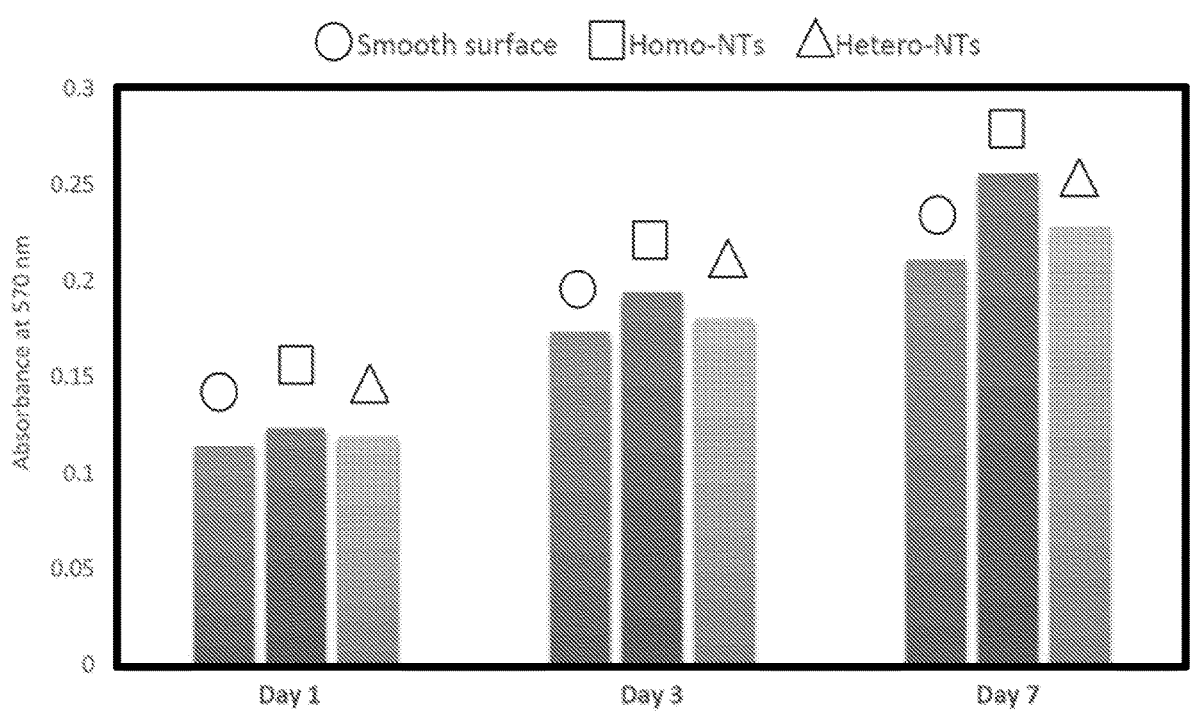
FIG. 7 shows Formazan absorbance from MTT cell viability assay for: 1) Ti-17Nb-6Ta smooth surface 2) with Homo-NTs, 3) with Hetero-NTs structures at different time intervals (1, 3 and 7 days), according to embodiments of the current invention.
Figure 8A:
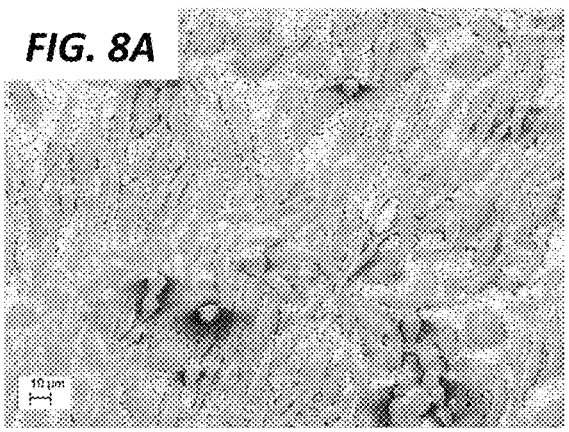
FIGS. 8A-8F show top-view FESEM images of endothelial cells grown on NTs surfaces after 3 days; (8A), (8C) and (8F) are cells grown on Homo-NTs at different magnification. (8B), (8D) and (8F) are cells grown on Hetero-NTs at different magnification, according to embodiments of the current invention.
Figure 8B:
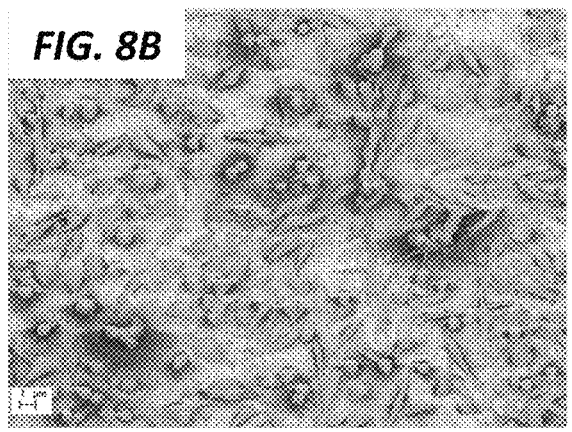
Figure 8C:
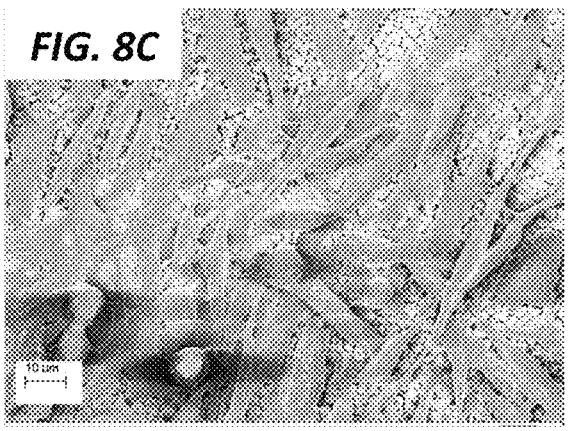
Figure 8D:
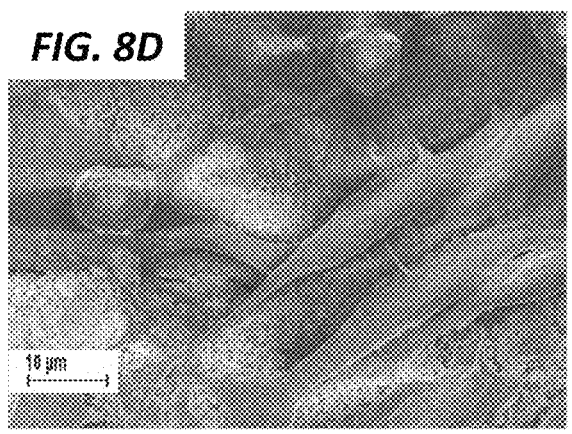
Figure 8E:
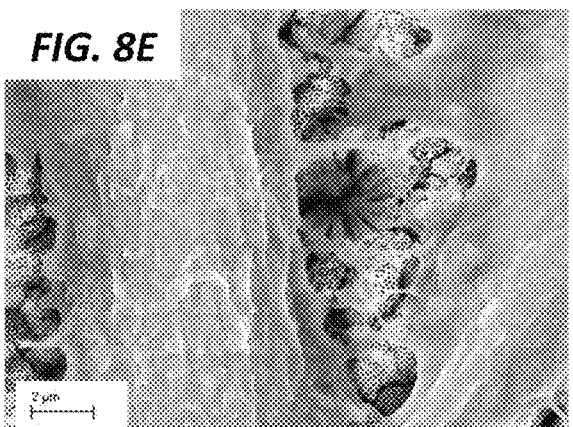
Figure 8F:
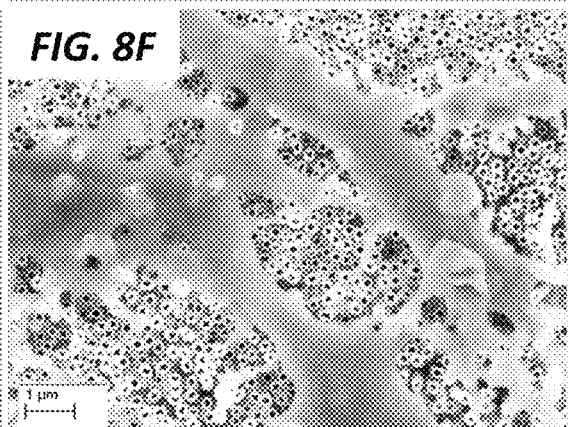

To confirm the trypan blue assay results, MTT assay was conducted for the same 3 types of samples: 1) Smooth surface of the as-received alloy, 2) Homo-NTs and 3) Hetero-NTs. The absorbance of the formazan solutions was reported as a reflection of viable cells concentration per sample, FIG. 7. Note the better outcome upon the use of nanoarchitectured surfaces as compared to the smooth surface. Also, Homo-NTs showed the same trend reported with trypan blue assay as the superior morphology for proliferation among the three tested samples.

Turning now to FESEM imaging of cells proliferation, endothelial cells were grown on the surface of Homo- and Hetero-NTs for 3 days to confirm the effect of dimensional homogeneity on the cells' proliferation. Cells were fixed and imaged using FESEM, FIGS. 8A-8F, confirming the superiority of Homo-NTs in guiding endothelialization over Hetero-NTs. Images (8A),(8C) and (8E) on the left side of FIG. 8, represent the cells' growth on Homo-NTs, where the island like structure of highly ordered nanotubes can be seen at the highest magnification (8E). While, images (8B), (8D) and (8F) on the right side of the figure illustrate cells on Hetero-NTs, where at the highest magnification (8F) NTs with different diameters can be observed. Elongated endothelial cells are predominantly seen on Homo-NTs, forming network like structure with more pronounced filopodial protrusions. This indicates better cells migration and proliferation on the homogeneous NTs structure, which would directly result in higher cells count as seen in the former assays. Cells cultured on Hetero-NTs, on the other hand, showed more rounded structure, less distribution on the surface and not yet crossing into a network. This indicates potentially slower healing rates for Hetero-NTs in applications.

For the drug loading and release, the platform according to the current invention delivers the drug only into the vascular tissue side and not the vessel lumen. Accordingly, anodized samples were tested for drug loading only on one side of the sheet covered with the NTs layer, to avoid interference or duplication of results from the other side. The results were compared between the two NTs morphologies to assess the system superiority, FIG. 9A. Note that the Homo-NTs drug loading capacity is almost double that of the Hetero-NTs, which can be related to the grooves found within the Homo-NTs between islands of compact nanotubes, FIG. 9B. These grooves can reach a width of 1 µm, which can act as a potential reservoir for larger amounts of drug. As described, Homo-NTs showed more promising results for both biological response as well as drug loading. Accordingly, it was further studied for its drug release profile using computational analysis.

Figure 9:
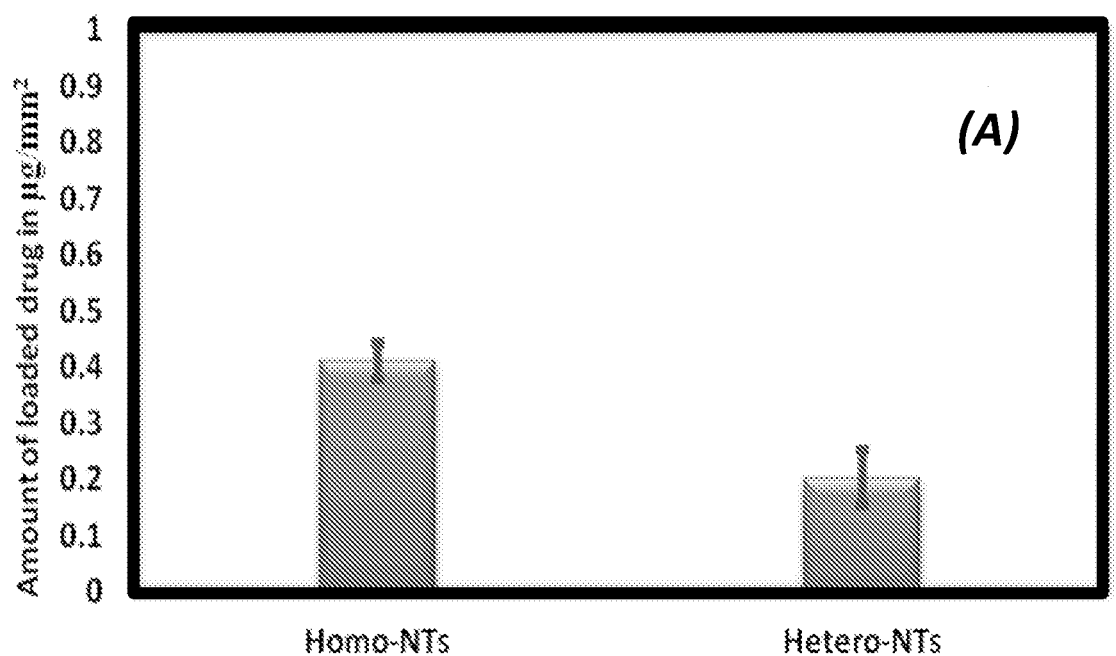
FIGS. 9A-9B show (9A) Comparison between drug loading capacity of Homo-NTs and Hetero-NTs, (9B) FESEM top-view image of Homo-NTs showing grooves between compact NTs islands, according to embodiments of the current invention.
Figure 9:
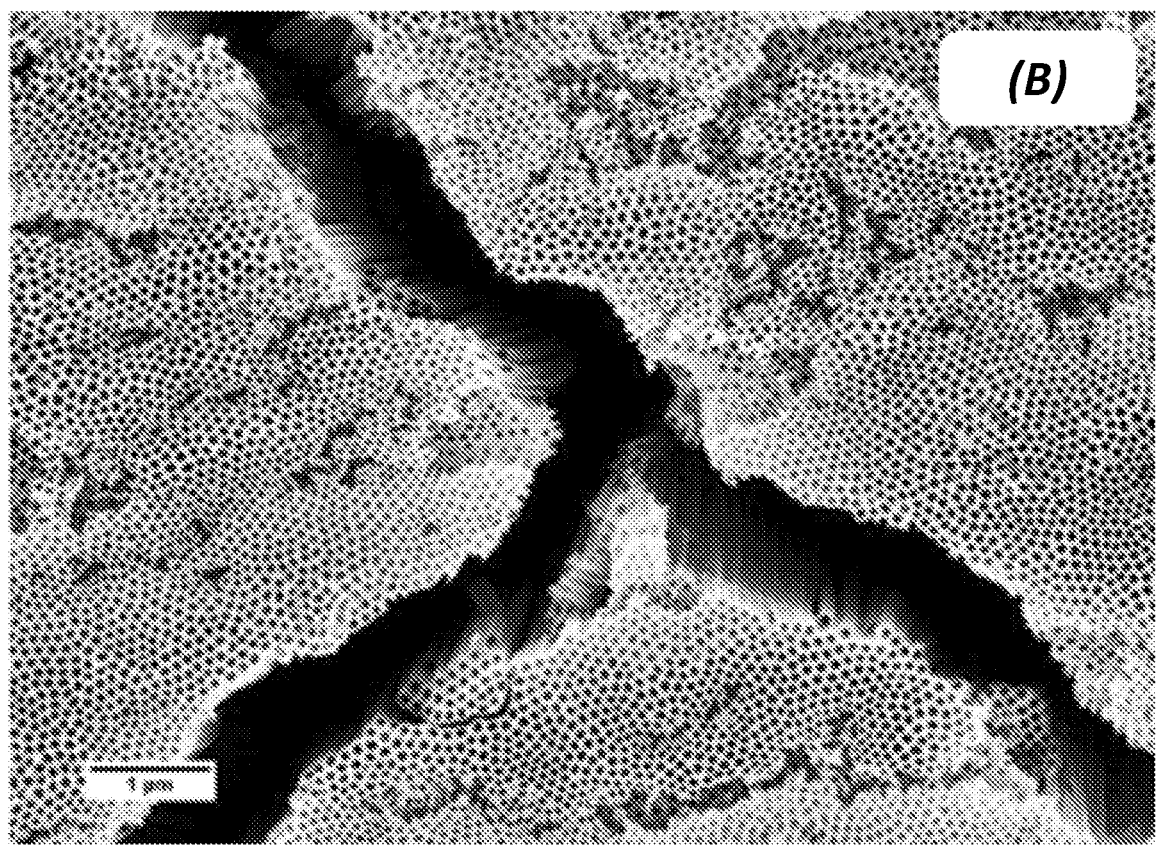
Figure 10A:
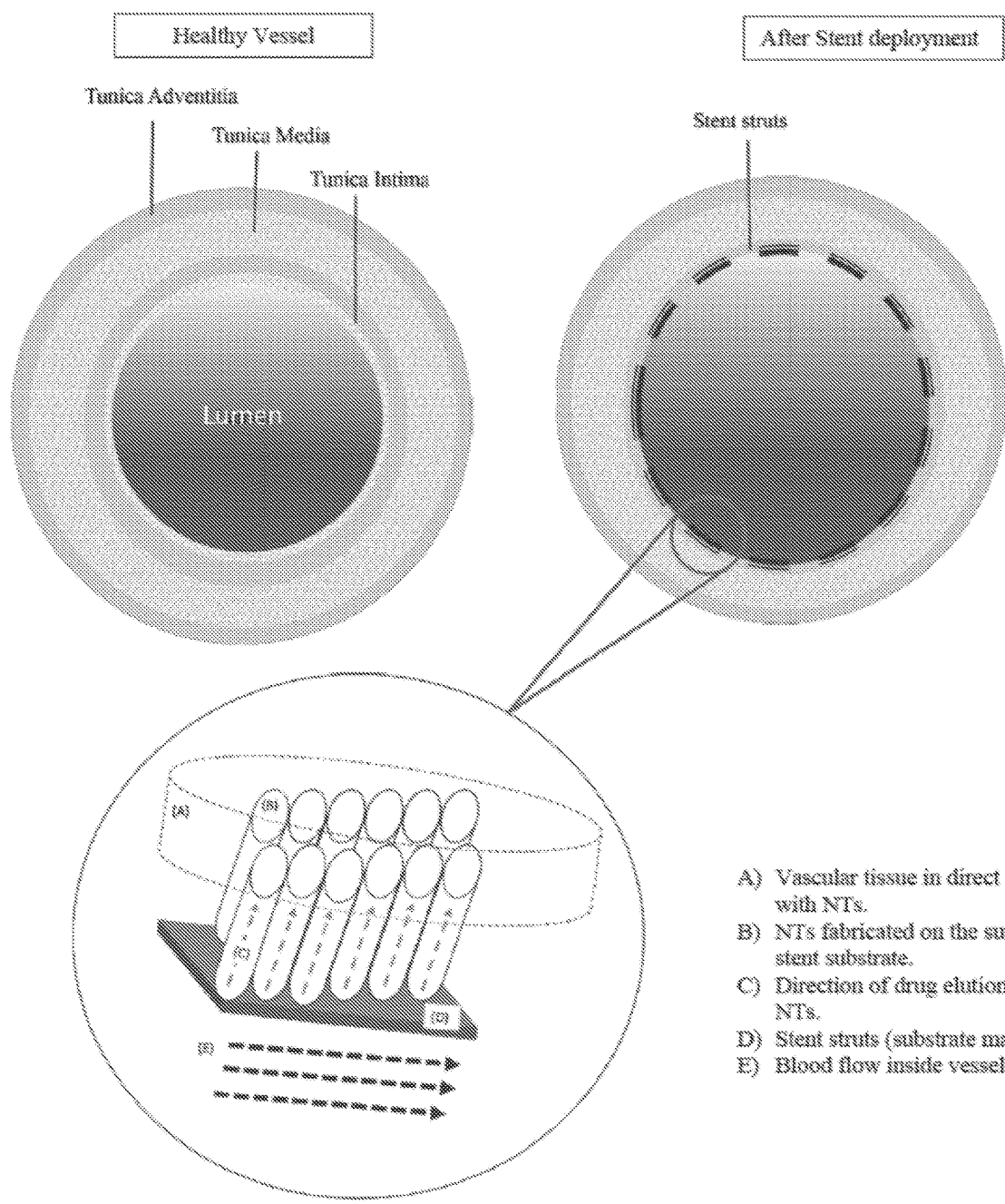
FIGS. 10A-10D show (10A) Illustration of physical model representing the NTs drug delivery system into vessel's tissue by use of a diagrammatic representation, not to scale, (10B) 2D geometry of the modeling domains for drug release from NTs, and (10C, 10D) the drug concentration over the modelling domain with A) 2D and B) 3D geometry at the end of simulation (3 days), according to embodiments of the current invention.
Figure 10B:
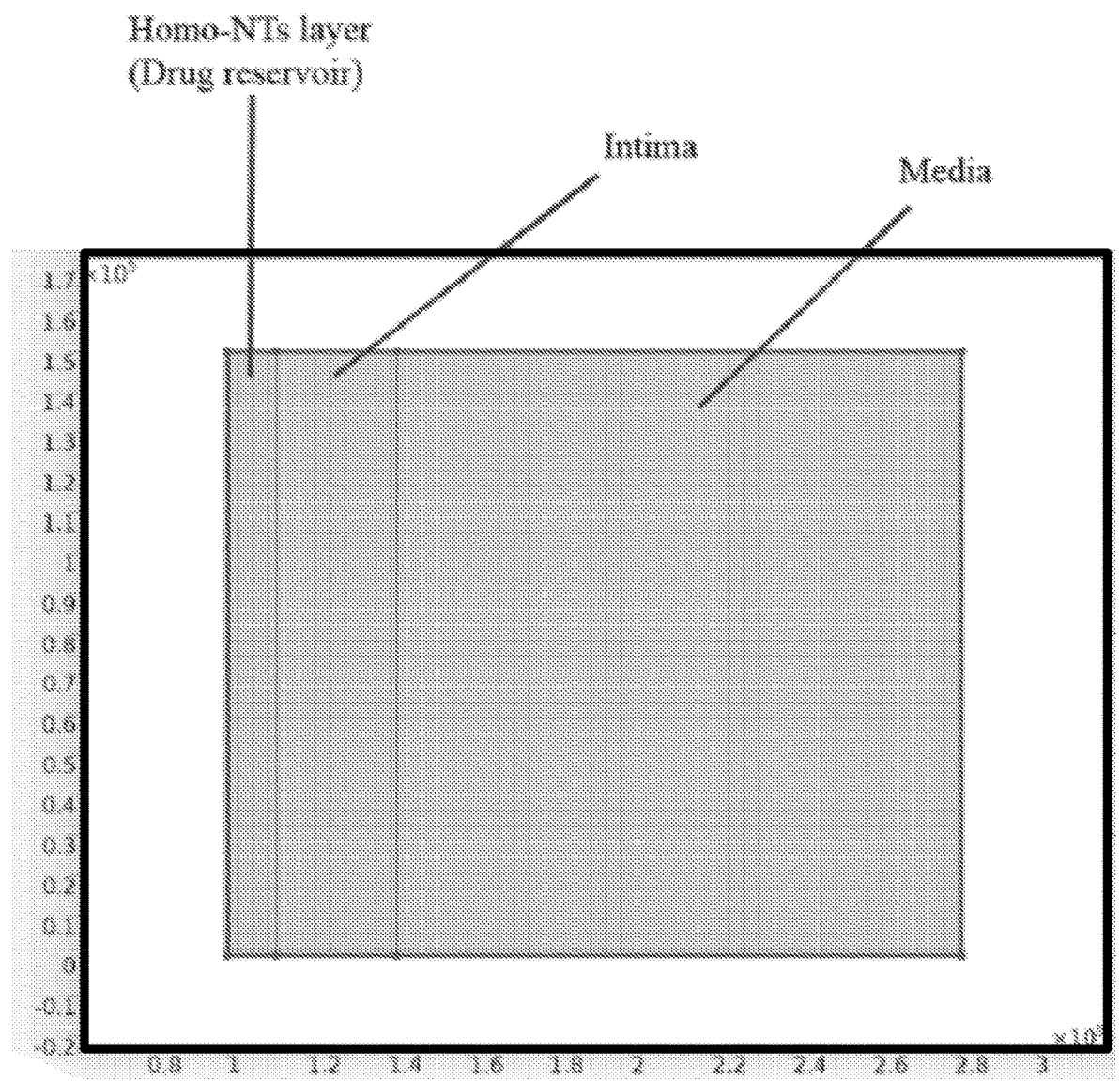
Figure 10C:
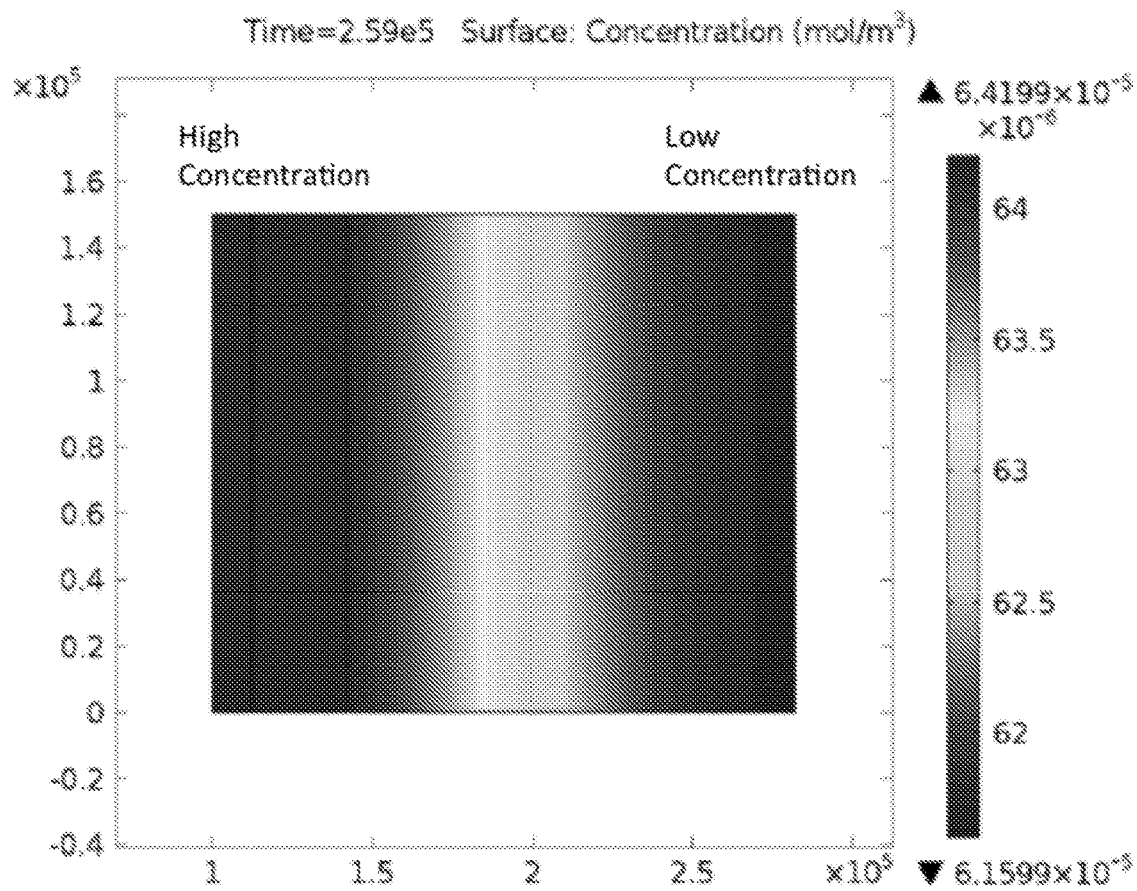
Figure 10D:
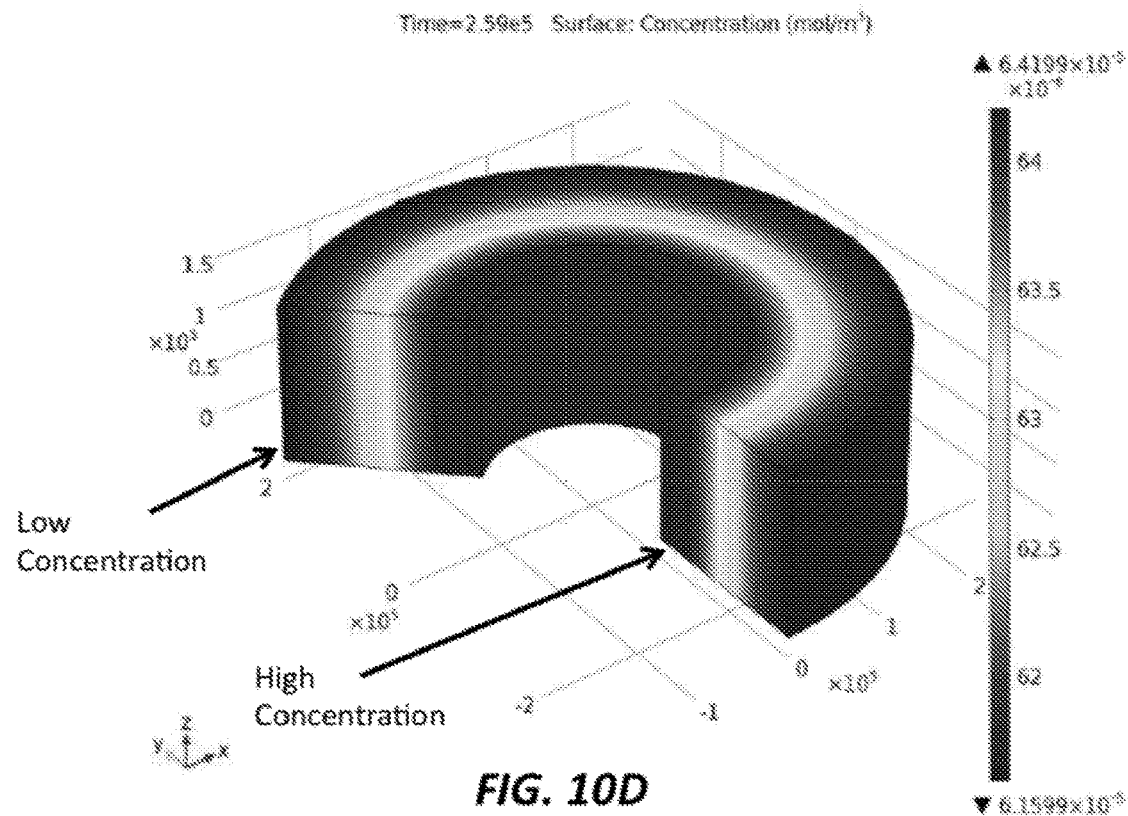

FIG. 10A shows a representation of the model used for the drug release system according to the current invention, where cross sections of the vessel at the healthy state (on the left) and after stenting (on the right) are shown. After stenting, metal struts are embedded into the intima with direct contact with the connective tissue, while endothelium is almost damaged. Atherosclerotic plaque is hypothetically considered to be totally removed during PTCA. The Homo-NTs are grown vertically on the Ti-alloy substrate, which are embedded in the vessel wall tissue. Drug release is intended to be in the direction of vessel wall only, hence not affected by the central blood flow in the vessel lumen. Therefore, mass transport in the model was identified to be dominated by diffusion and excluded both convection and migration. Drug release was assumed to be restricted to the surrounding tissue moving across the connective tissue of Intima layer—as endothelium lining is damaged—and into the Media. Boundary conditions were therefore described to restrict the flux within that system and indicate that flux outside its boundaries is equal to zero (n. Ni=0). Accordingly, the model geometry was built as shown in FIG. 9B with 2D spatial dimension, comprising the modeling domains within the system boundaries; the NTs and Intima layer (excluding damaged endothelium and Media layer). The simulation parameters were identified reference to previously reported practical results for nanotubes diameters and same loaded drug. Materials of the model domain were identified according to their diffusion coefficient ($D_c$). For Intima, $D_c$ is $=5.4\times10^{-12}$ m$^2$/sec and for Media $D_c$ is $=5.0\times10^{-14}$ m$^2$/sec. This difference in D can directly affect the drug elution, as diffusion coefficient can be the rate limiting step for mass transport across the system. Diffusion coefficient of the drug in the NTs was calculated using equation (1):

$$\sqrt{\frac{M_t}{M_o \times 2}} = \frac{Dt}{\pi h^2} \quad (1)$$

where $M_t$ is the amount of drug released at time t, $M_o$ is the initial drug amount, and h is the layer thickness. The calculated value of the drug diffusion coefficient was found to be $=2.5\times10^{-11}$ m$^2$/s. Using the aforementioned parameters, a time dependant study was designed for the drug release profile. FIGS. 10C-10D show drug concentration across the modeling domains, using the 2D geometry and its 3D representation by axial symmetry at the end of the simulation (3 days). These figures show the higher drug concentration, and the lower concentrations.

Figure 11:
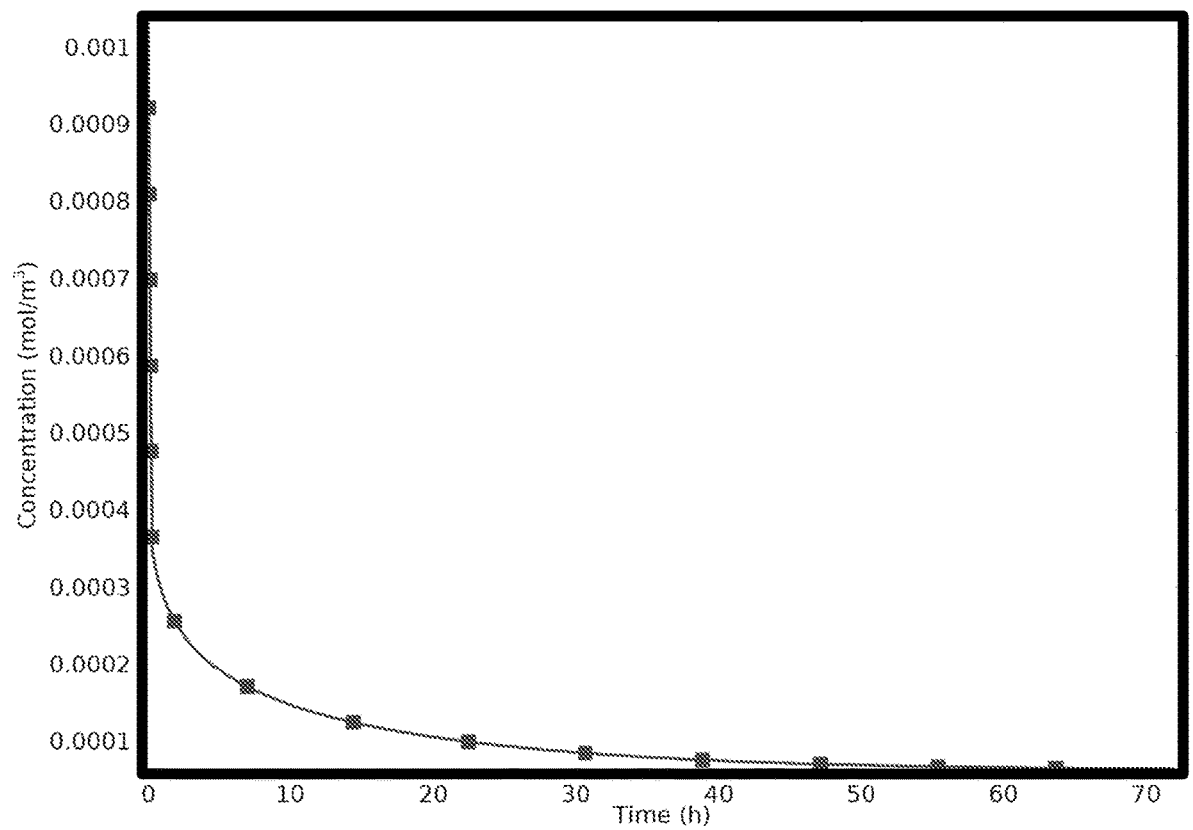
FIG. 11 shows the calculated drug concentration in the NTs over time, according to embodiments of the current invention.

The time-dependant estimation of the drug released was used to plot the drug concentration in the NTs over time. As seen in FIG. 11, almost 100% of the initial drug amount was released after 3 days. For DES, this rate can be considered faster than required, in reference to one month with polymeric coating. Further control over the system can be enabled by, for example, using drug carriers or external fields. However, other factors may have resulted in such relatively fast rate other than the inherent properties of the NTs system. This may include the initial amount of loaded drug. It is assumed that drug loading may increase by increasing the initially added drug and the techniques used for loading other than static solutions. This may not only increase the total amount of drug released but also the elution rate. Also, the nature of the drug is a critical factor in such context. The tested drug (2'-deoxyadenosine) is hydrophilic with lower diffusion coefficient than hydrophobic drugs used mainly in the market. Extending the measurement into hydrophobic molecules with lower diffusivity may slow down the rate and sustain the release.

In summary, a biologically active, and possibly drug bearing system was presented to replace polymeric coating on stent as surface modification. This system comprises self-grown nanoarchitectures for Ni-free Ti-17Nb-6Ta at. % alloy that is potential for the use in fabricating self-expandable stents. Two exemplary nanotubes (NTs) morphologies were successfully fabricated from the same substrate using anodization technique: 1) Homo-NTs, characterized by highly ordered, vertically aligned nanotubes of uniform and homogeneous tubes diameter, closely packed into islands separated by grooves, and 2) Hetero-NTs, characterized by highly ordered, vertically aligned nanotubes but of non-uniform and heterogeneous tubes diameter, yet evenly distributed along the substrate. XRD and Raman analysis for the as anodized samples indicated the formation of the anatase phase associated with annealed titania NTs. Possible overlapping of peaks from other alloying materials (Nb and Ta), hindered accurate compositional analysis using those two techniques. Therefore, XPS, as more sensitive and highly powerful technique for compositional analysis, confirmed the formation of mixture oxides of the alloying materials on the surface without losing one of the elements during anodization. Using nanoindentation technique, Homo-NTs showed the higher hardness, while Hetero-NTs gave higher stiffness values. The MTT assay indicated that both NTs morphologies as well as the substrate material had no cytotoxicity and were ready for further biological investigation. Also, the proliferation studies showed significantly better results for endothelial cells proliferation upon using the NTs compared to their smooth counterpart. Furthermore, Homo-NTs showed superior activity than Hetero-NTs regarding biological response. Drug loading capacity were practically investigated and compared for the two morphologies using 2'-Deoxyadenosine drug. And results were as well in favour of Homo-NTs, which showed higher amount of drug retained from initially added concentration. The drug release profile for this system was then simulated and calculated through computational studies using COMSOL Multiphysics software with transport of diluted species module. Within a diffusion controlled physical model, a time dependent study calculated drug concentration released from the NTs into the tissue across time. It was presented that almost 100% of the practically loaded amount would be eluted from the NTs within a 3 day duration.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example the mechanical properties (i.e. Yield strength, Ultimate tensile strength, Hardness, Elongation, Young's modulus and Wear resistance) of the present Ti-17Nb-6Ta at. % alloy may be controlled through different thermomechanical treatments to provide wide range of mechanical performance of the stent. All such variations are considered to be within the scope and spirit of the present invention as defined by the following claims and their legal equivalents.

What is claimed:

1. A drug eluting stent, comprising:
    a) a stent having a biocompatible composition consisting essentially of Ti-17Nb-6Ta alloy; and
    b) nanotubes having a composition consisting essentially of Ti-17Nb-6Ta oxide attached by self-growth on an inner wall of said Ti-17Nb-6Ta alloy stent, wherein said Ti-17Nb-6Ta oxide nanotubes are configured for holding and releasing drugs to enable enhanced endothelialization during tissue healing, wherein said Ti-17Nb-6Ta oxide nanotubes are homogenous nanotubes or heterogeneous nanotubes, wherein said homogeneous nanotubes comprise a Young's Modulus in a range of 16-27 GPa, wherein said homogeneous nanotubes hold up to 0.45 μg/mm$^2$ of a loaded drug, wherein said heterogeneous nanotubes comprise a Young's Modulus in a range of 18-23 GPa, wherein said heterogeneous nanotubes hold up to 0.25 μg/mm$^2$ of a loaded drug.

2. The drug eluting stent according to claim 1, wherein said Ti-17Nb-6Ta oxides nanotubes are organized in a vertical orientation relative to said inner wall of said Ti-17Nb-6Ta stent with variable oxide nanotube morphologies.

3. The drug eluting stent according to claim 1, wherein said Ti-17Nb-6Ta stent comprises a self-expanding Ti-17Nb-6Ta alloy stent.

4. The drug eluting stent according to claim 1, wherein said Ti-17Nb-6Ta oxides nanotubes comprise an inner diameter in a range of 65 nm to 85 nm with variable drug loading capacity.

5. The drug eluting stent according to claim 1, wherein said Ti-17Nb-6Ta oxides nanotubes comprise a length in a range of up to 14 μm for variable drug loading capacity.

6. The drug eluting stent according to claim 1, wherein said Ti-17Nb-6Ta alloy stent and said Ti-17Nb-6Ta oxides nanotubes are Ni-free and biocompatible and non-toxic to a human host.

* * * * *